US00PP28001P2

(12) United States Plant Patent
Williams

(10) Patent No.: US PP28,001 P2
(45) Date of Patent: May 9, 2017

(54) ***COLOCASIA* PLANT NAMED 'MAXIMUS GIGANTE'**

(50) Latin Name: ***Colocasia* hybrid**
Varietal Denomination: Maximus Gigante

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 81 days.

(21) Appl. No.: 14/545,437

(22) Filed: May 4, 2015

(51) Int. Cl.
*A01H 5/12* (2006.01)

(52) U.S. Cl.
USPC ..... Plt./373

(58) Field of Classification Search
USPC ..... Plt./373, 226, 263.1, 258
See application file for complete search history.

(56) References Cited

PUBLICATIONS

Brians Botanicals *Colocasia* Maximus Gigante ppaf, retrieved on Sep. 7, 2016, retrieved from the Internet at <http://briansbotanicals.us/index.php/plant-catalog/hybrids/colocasia-maximus-gigante-ppaf-detail> 1 p.*

National Gardening Association Elephant's Ear (*Colocasia* 'Maximus Gigante') in the Elephant Ears (*Colocasia*) Database 2016, retrieved on Sep. 7, 2016, retrieved from the Internet at <http://garden.org/plants/view/659551/Elephants-Ear-Colocasia-Maximus-Gigante/> 3 pp.*

Rush Creek Growers, Inc. Wholesale Catablo 2015, retrieved on Sep. 8, 2016, retrieved from the Internet at <http://www.rushcreekgrowers.com/_ccLib/downloads/2015+Catalog--online+version.pdf> p. 77.*

* cited by examiner

*Primary Examiner* — June Hwu
(74) *Attorney, Agent, or Firm* — Penny J. Aguirre

(57) ABSTRACT

A new cultivar of *Colocasia* plant named 'Maximus Gigante', that is characterized by its clump forming, large plant habit growing up to 2.1 m in height, its large leaves up to 1 m in length that are held nearly horizontally, its leaves that are green in color with a pinkish-purple marking where the stem attaches and dark bluish-purple colored markings between the veins, its leaves with lower surfaces maroon-gray to green in color, its petioles that are dark green to bluish gray in color, suffused with pink at the edges, its healthy root system that is cold hardy up to U.S.D.A. Zone 7, and its production of very large tubers as it ages.

3 Drawing Sheets

Botanical classification: *Colocasia* hybrid.
Cultivar designation: 'Maximus Gigante'.

BACKGROUND OF THE INVENTION

The present invention, *Colocasia* 'Maximus Gigante', relates to a new and distinct interspecific hybrid of *Colocasia*, hereinafter referred to by its cultivar name, 'Maximus Gigante'. 'Maximus Gigante' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are colorful and well suited for landscape or container growth. 'Maximus Gigante' arose from a cross make in August of 2012 between an unnamed plant of *Colocasia esculenta*×*gaoligongensis* (not patented) as the female parent and an unnamed plant of *Leucocasia gigantea* plant (not patented) as the male parent. 'Maximus Gigante' was selected as a single unique plant in July of 2013 from amongst the seedlings derived from the above cross.

Asexual propagation of the new cultivar was first accomplished by in vitro propagation, specifically meristematic cell tissue culture, under the direction of the Inventor in Eustis, Fla. in February of 2014. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Maximus Gigante' as a new and unique cultivar of *Colocasia*.

1. 'Maximus Gigante' exhibits a clump forming, large plant habit growing up to 2.1 m in height.
2. 'Maximus Gigante' exhibits large leaves up to 1.2 m in length and are held nearly horizontally.
3. 'Maximus Gigante' exhibits leaves that are green in color with a pinkish-purple marking where the stem attaches and dark bluish-purple colored markings between the bright green veins.
4. 'Maximus Gigante' exhibits leaves with lower surfaces maroon-gray to green in color.
5. 'Maximus Gigante' exhibits petioles that are dark green to bluish gray in color, suffused with pink at the edges.
6. 'Maximus Gigante' exhibits a healthy root system that is root hardy up to U.S.D.A. Zone 7.

7. 'Maximus Gigante' exhibits the production of very large tubers as it ages.

The female parent of 'Maximus Gigante', differs from 'Maximus Gigante' in having leaves that are shorter in length, with a black marking where the stem attaches to the leaf and dark areas between the veins that fade with age, in having a spreading habit with running rhizomes, in being root hardy to U.S.D.A Zone 6, and in producing mid-sized tubers. The male parent of 'Maximus Gigante', differs from 'Maximus Gigante' in having leaves that are larger in size and uniformly green in color with no center marking or coloration between veins, in having petioles that are brown in color, and in having a taller plant height. 'Maximus' can be most closely compared to the *Colocasia* cultivar 'Illustris' (not patented). 'Illustris' differs from 'Maximus Gigante' in having a shorter in height, in having leaves that are shorter in length and black leaves with green veins, in having petioles that are green in color, in having a quickly spreading plant habit with underground runners, and in producing smaller tubers.

BRIEF DESCRIPTION OF THE DRAWINGS

The accompanying colored photographs illustrate the overall appearance and distinct characteristics of the new *Colocasia*, 'Maximus Gigante'. The photographs were taken of two year-old plants as grown outdoors, in full sun, under two-millimeter poly in Louisville, Ky.

The photograph in FIG. 1 provides an overall view of the maturing foliage and plant habit of 'Maximus Gigante'.

Figure 1:
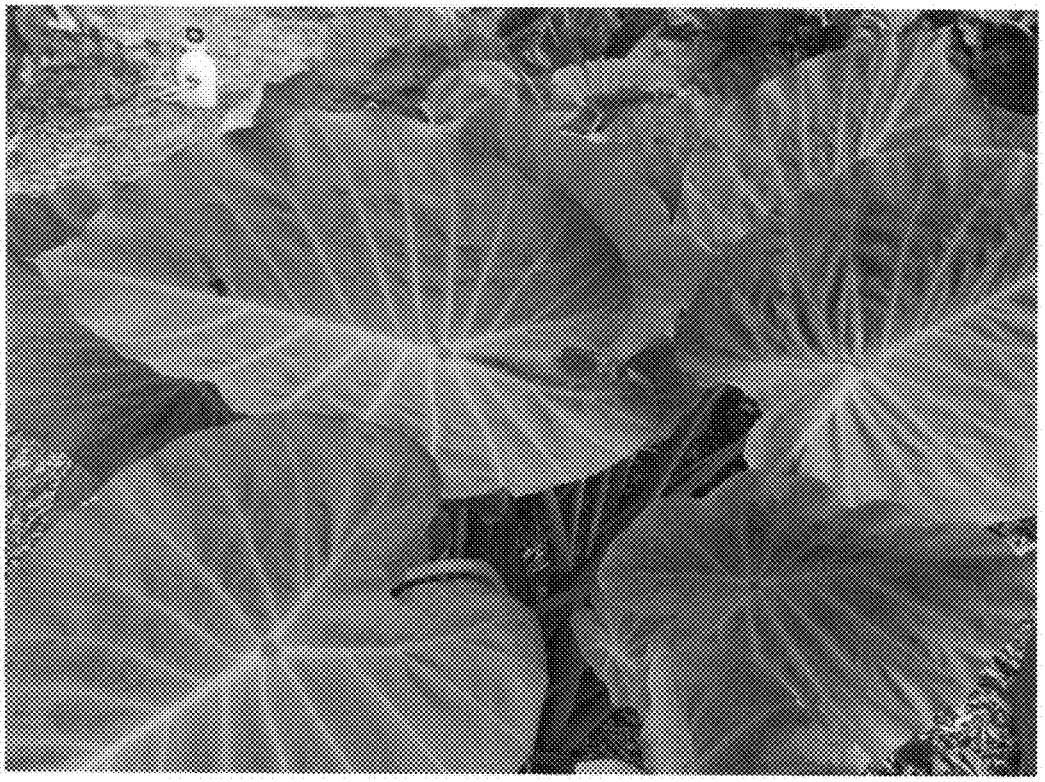
Figure 2:
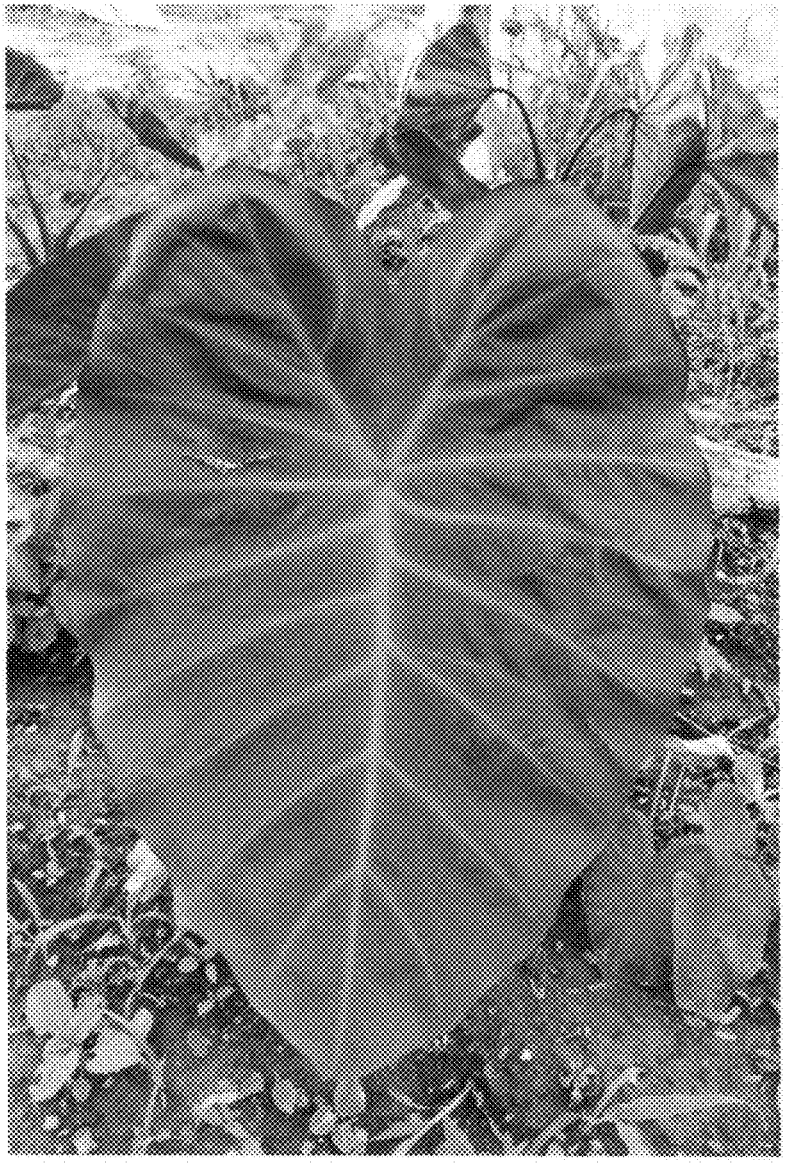

The photograph in FIG. 2 provides a close-up view of a mature leaf of 'Maximus Gigante'.

Figure 3:
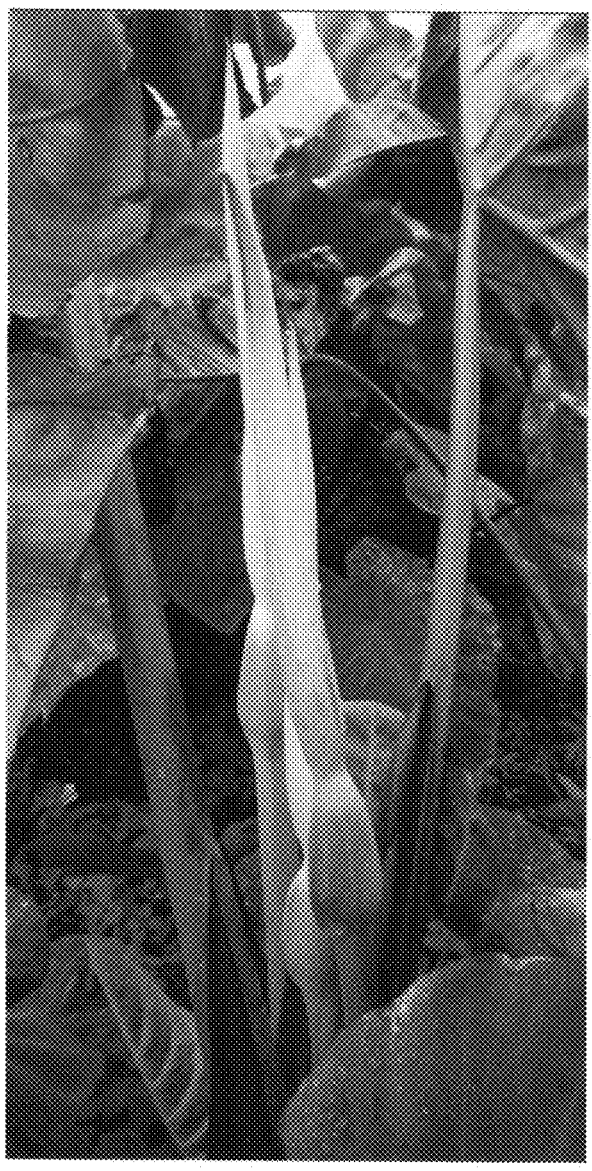

The photograph in FIG. 3 provides a view of the petioles and blooming stalks of 'Maximus Gigante'.

The colors in the photographs are as close as possible with the digital photography techniques available, the color values cited in the detailed botanical description accurately describe the colors of the new *Colocasia*.

DETAILED BOTANICAL DESCRIPTION OF THE PLANT

The following is a detailed description of three year-old plants of the new cultivar plants as grown outdoors, in full sun, under two-millimeter poly in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid summer until frost in Kentucky.

*Plant type.*—Tropical perennial herb.

*Plant habit.*—Upright, stemless.

*Height and spread.*—Reaches up to 2.1 m in height and 2.5 m in width.

*Cold hardiness.*—At least to U.S.D.A. Zone 7.

*Diseases and pests.*—No resistance and susceptibility to diseases or pests has been observed.

*Roots.*—Fleshy, 155A in color, strong and healthy root system.

*Propagation type.*—In vitro propagation.

*Rooting.*—Root initiation of tissue culture plantlet; 14 to 35 days, time to produce a young rooted plant; 14 to 42 days.

*Growth rate.*—Vigorous.

*Stem description.*—Stemless, can produce tubers with age at base of petiole.

*Tubers.*—Formed at the base of the petioles with age, about 28.5 cm in length and 18.3 cm in width on a 2 year-old plant, comprised of petiole scales, surface is rough and paper-like, color is a blend of N199B and 197A.

Foliage description:

*Leaf shape.*—Ovate.

*division.*—Single.

*Leaf base.*—Cordate, sinus depth about 2.54 cm.

*Leaf apex.*—Acute and cuspidate.

*Leaf venation.*—Pinnate, color: young and mature upper surface a blend of N144C and 144A with a spot 187A in color at petiole attachment on the mature upper leaf surface, young lower surface 144D, mature lower surface 144D and suffused with 183A.

*Leaf margins.*—Entire and slightly undulate.

*Leaf attachment.*—Petiolate.

*Leaf arrangement.*—Single.

*Leaf surface.*—Upper surface and lower surface; coriaceous and glabrous.

*Leaf orientation.*—Nearly horizontal.

*Leaf color.*—Young foliage: upper surface; 143A and lightly suffused with N187B and lower surface; 191A to 191B and slightly suffused with N187B, mature foliage upper surface; a blend of 143B and N187A to N187B between the veins, mature foliage lower surface a blend of 191A to 191B and N187B between the veins.

*Leaf size.*—An average of 1 m in length and 61 cm in width.

*Leaf sinus depth.*—Average of 8.32 cm.

*Petioles.*—Held erect to semi-erect, an average of 38 cm in length and 4 mm in distal diameter and 15 mm in proximal diameter, glaucescent surface, color; blend of 144D and 189A and suffused with 183A on edges, the basal sheath portion is triangular in shape, N77A in color on outer surface and 189A in color on the inner surface, 5 cm in diameter and 8 cm in length, glabrous on both surfaces and glossy surface on the outer surface.

Inflorescence description:

*Inflorescence type.*—Spadix surrounded by a spathe, male portion held above female portion, only female flowers were developed.

*Inflorescence size.*—Average of 25.6 cm in length and 2 cm in width.

*Inflorescence bud.*—Linear to slightly narrow oblanceolate in shape, an average of 25.6 cm in length, male portion; 2 cm in width, female portion; 3.3 cm in width, male portion; 150D in color and female portion; 145B.

*Flower fragrance.*—None.

*Lastingness of inflorescence.*—Inflorescence blooms intermittently during the bloom period, individual flowers last about 4 to 6 days.

*Inflorescence/flower quantity.*—Intermittent throughout the bloom season in sets of 3 or more, an average of 270 female flowers per spadix, male flowers were undeveloped.

*Spathe.*—Hooded, bract, subtending spadix, does not fully open to expose spadix, elliptic in shape, entire margin, acute apex, 18.6 cm in length and 8 cm in width, inner surface; coriaceous and smooth, outer surface; coriaceous and textured with linear grooves, lasts 5 to 7 days, color: when opening and fully open on inner rear surface 155A and outer rear surface; a blend of 150D and 155A.

*Spadix.*—Male portion above female zone, upright cylindrical shape (phallus-like), apex narrowly pointed, about 9 mm in diameter (not including ovary) and 13.2 cm in length, male zone; 9 mm in diameter and 9.5 cm in length, color immature and mature 150D, female zone; 2 cm in diameter and 3.7 length, color immature and mature 144C with 150D at the tips.

*Peduncle.*—Triangular in shape, grows from base of plant, up to 30.5 cm in length and 2 cm in diameter, held nearly vertical, durable and strong, 145A in color, glabrous surface.

Reproductive organs:

*Gynoecium.*—1 pistil, 5 stigmas are 150D in color, ovary is flattened obovate in shape and 144C in color.

*Androecium.*—Undeveloped.

*Fruit and seed.*—Sterile.

It is claimed:

1. A new and distinct cultivar of *Colocasia* plant named 'Maximus Gigante' as herein illustrated and described.

* * * * *